United States Patent
Peterson et al.

(10) Patent No.: US 7,547,315 B2
(45) Date of Patent: Jun. 16, 2009

(54) MECHANICAL METHOD AND APPARATUS FOR TISSUE FASTENING

(75) Inventors: James A. Peterson, Edina, MN (US); Christopher J. Sperry, Plymouth, MN (US); Joseph M. Gryskiewicz, Edina, MN (US); Delmer L. Smith, Edina, MN (US)

(73) Assignee: Incisive Surgical, Inc., Plymouth, MN (US)

( * ) Notice: Subject to any disclaimer, the term of this patent is extended or adjusted under 35 U.S.C. 154(b) by 727 days.

(21) Appl. No.: 11/003,145

(22) Filed: Dec. 3, 2004

(65) Prior Publication Data

US 2005/0085857 A1    Apr. 21, 2005

Related U.S. Application Data

(60) Continuation of application No. 10/448,838, filed on May 30, 2003, which is a division of application No. 10/179,628, filed on Jun. 25, 2002, now Pat. No. 6,726,705, application No. 11/003,145, which is a continuation-in-part of application No. 10/607,497, filed on Jun. 25, 2003, and a continuation-in-part of application No. 10/603,397, filed on Jun. 25, 2003, now Pat. No. 7,112,214.

(51) Int. Cl.
*A61B 17/08* (2006.01)
*A61D 1/00* (2006.01)

(52) U.S. Cl. .................... 606/213; 606/216; 227/175.1; 227/176.1

(58) Field of Classification Search ................. 606/142, 606/219, 216–218; 227/175.1
See application file for complete search history.

(56) References Cited

U.S. PATENT DOCUMENTS 2,283,814 A    5/1942    La Place (Continued)

FOREIGN PATENT DOCUMENTS

EP    1 323 384 A2    7/2003

OTHER PUBLICATIONS

Brochure: *Information Booklet for Auto Suture® Purse String Instrument*, Auto Suture Company, a division of United States Surgical Corporation, Norwalk, CT, 2 pgs., 1978.

(Continued)

*Primary Examiner*—Todd E Manahan
*Assistant Examiner*—Michael G Mendoza
(74) *Attorney, Agent, or Firm*—Patterson, Thuente, Skaar & Christensen, P.A.

(57) ABSTRACT

A mechanical system for sequentially securing skin tissue preferably utilizes a tissue manipulator apparatus to approximate a portion of an interior surface of each of two pieces of living dermis tissue along a vertical interface below an exterior surface such that discrete target tissue zones are defined within the two pieces of living dermis tissue. An applicator apparatus includes a driving head portion positioned in the vertical interface and at least partially below the exterior surface and a handle portion positioned at least partially above the exterior surface. The applicator apparatus unilaterally drives a fastener through a first side of the living dermis tissue and then sequentially drives the fastener through a second side of the living dermis such that the fastener is positioned below the exterior surface and a portion of the fastener is positioned generally transverse to the vertical interface. The manipulator apparatus and the applicator apparatus can be arranged to be integral components operably connected together as part of a hand-held instrument capable of carrying and deploying fasteners.

8 Claims, 12 Drawing Sheets

U.S. PATENT DOCUMENTS

| | | |
|---|---|---|
| 2,351,608 A | 6/1944 | Greenwood |
| 2,439,383 A | 4/1948 | Erickson |
| 2,526,902 A | 10/1950 | Rublee |
| 2,881,762 A | 4/1959 | Lowrie |
| 2,959,172 A | 11/1960 | Held |
| 3,082,426 A | 3/1963 | Miles |
| 3,123,077 A | 3/1964 | Alcamo |
| 3,297,033 A | 1/1967 | Schmitt et al. |
| 3,344,790 A | 10/1967 | Dorner |
| 3,636,956 A | 1/1972 | Schneider |
| 3,643,851 A | 2/1972 | Green et al. |
| 3,716,058 A | 2/1973 | Tanner, Jr. |
| 3,757,629 A | 9/1973 | Schneider |
| 3,792,010 A | 2/1974 | Wasseman et al. |
| 4,014,492 A | 3/1977 | Rothfuss |
| 4,027,676 A | 6/1977 | Mattei |
| 4,047,533 A | 9/1977 | Perciaccante et al. |
| 4,162,678 A | 7/1979 | Fedotov et al. |
| 4,259,959 A | 4/1981 | Walker |
| 4,261,244 A | 4/1981 | Becht et al. |
| 4,317,451 A | 3/1982 | Cerwin et al. |
| 4,399,810 A | 8/1983 | Samuels et al. |
| 4,407,286 A | 10/1983 | Noiles et al. |
| 4,410,125 A | 10/1983 | Noiles et al. |
| 4,428,376 A | 1/1984 | Mericle |
| 4,430,998 A | 2/1984 | Harvey et al. |
| 4,434,796 A | 3/1984 | Karapetian et al. |
| 4,454,875 A | 6/1984 | Pratt et al. |
| 4,467,805 A | 8/1984 | Fukuda |
| 4,485,816 A | 12/1984 | Krumme |
| 4,485,953 A | 12/1984 | Rothfuss |
| 4,493,322 A | 1/1985 | Becht |
| 4,505,273 A | 3/1985 | Braun et al. |
| 4,506,669 A | 3/1985 | Blake, III |
| 4,508,253 A | 4/1985 | Green |
| 4,526,173 A | 7/1985 | Sheehan |
| 4,526,174 A | 7/1985 | Froehlich |
| 4,534,352 A | 8/1985 | Korthoff |
| 4,535,772 A | 8/1985 | Sheehan |
| 4,557,265 A | 12/1985 | Andersson |
| 4,566,620 A | 1/1986 | Green et al. |
| 4,568,009 A | 2/1986 | Green |
| 4,570,623 A | 2/1986 | Ellison et al. |
| 4,573,622 A | 3/1986 | Green et al. |
| 4,583,670 A | 4/1986 | Alvarado |
| 4,592,498 A | 6/1986 | Braun et al. |
| 4,593,843 A | 6/1986 | Saravis |
| 4,596,350 A | 6/1986 | Smith et al. |
| 4,607,638 A | 8/1986 | Crainich |
| 4,610,251 A | 9/1986 | Kumar |
| 4,618,086 A | 10/1986 | Li et al. |
| 4,619,262 A | 10/1986 | Taylor |
| 4,637,380 A | 1/1987 | Orejola |
| 4,646,741 A | 3/1987 | Smith |
| 4,655,222 A | 4/1987 | Florez et al. |
| 4,665,916 A | 5/1987 | Green |
| 4,671,279 A | 6/1987 | Hill |
| 4,676,245 A | 6/1987 | Fukuda |
| 4,696,300 A | 9/1987 | Anderson |
| 4,719,917 A | 1/1988 | Barrows et al. |
| 4,728,020 A | 3/1988 | Green et al. |
| 4,741,337 A | 5/1988 | Smith et al. |
| 4,752,024 A | 6/1988 | Green et al. |
| 4,753,636 A | 6/1988 | Free |
| 4,762,260 A | 8/1988 | Richards et al. |
| 4,776,506 A | 10/1988 | Green |
| 4,789,090 A | 12/1988 | Blake, III |
| 4,802,478 A | 2/1989 | Powell |
| 4,887,601 A | 12/1989 | Richards |
| 4,887,756 A | 12/1989 | Puchy |
| 4,895,148 A | 1/1990 | Bays et al. |
| 4,899,745 A | 2/1990 | Laboureau et al. |
| 4,915,100 A | 4/1990 | Green |
| 4,924,866 A | 5/1990 | Yoon |
| 4,955,898 A | 9/1990 | Matsutani et al. |
| 4,969,591 A | 11/1990 | Richards et al. |
| 4,976,686 A | 12/1990 | Ball et al. |
| 4,976,715 A | 12/1990 | Bays et al. |
| 4,994,073 A | 2/1991 | Green |
| 5,002,562 A | 3/1991 | Oberlander |
| 5,007,921 A | 4/1991 | Brown |
| 5,015,252 A | 5/1991 | Jones |
| 5,026,390 A | 6/1991 | Brown |
| 5,035,692 A | 7/1991 | Lyon et al. |
| 5,044,540 A | 9/1991 | Dulebohn |
| 5,047,047 A | 9/1991 | Yoon |
| 5,058,315 A | 10/1991 | Wagner |
| 5,062,563 A | 11/1991 | Green et al. |
| 5,078,731 A | 1/1992 | Hayhurst |
| 5,080,665 A | 1/1992 | Jarrett et al. |
| 5,089,009 A | 2/1992 | Green |
| 5,108,422 A | 4/1992 | Green et al. |
| 5,129,570 A | 7/1992 | Schulze et al. |
| 5,156,609 A | 10/1992 | Nakao et al. |
| 5,158,566 A | 10/1992 | Pianetti |
| 5,158,567 A | 10/1992 | Green |
| 5,160,339 A | 11/1992 | Chen et al. |
| 5,179,964 A | 1/1993 | Cook |
| 5,211,644 A | 5/1993 | VanBeek et al. |
| 5,211,722 A | 5/1993 | Wagner |
| 5,236,440 A | 8/1993 | Hlavacek |
| 5,257,713 A | 11/1993 | Green et al. |
| 5,258,009 A | 11/1993 | Conners |
| 5,258,010 A | 11/1993 | Green et al. |
| 5,258,012 A | 11/1993 | Luscombe et al. |
| 5,263,973 A | 11/1993 | Cook |
| 5,269,783 A | 12/1993 | Sander |
| 5,269,792 A | 12/1993 | Kovac et al. |
| 5,285,944 A | 2/1994 | Green et al. |
| 5,292,326 A | 3/1994 | Green et al. |
| 5,293,881 A | 3/1994 | Green et al. |
| 5,297,714 A | 3/1994 | Kramer |
| 5,324,307 A | 6/1994 | Jarrett et al. |
| 5,337,937 A | 8/1994 | Remiszewski et al. |
| 5,342,376 A | 8/1994 | Ruff |
| 5,350,400 A | 9/1994 | Esposito et al. |
| 5,364,003 A | 11/1994 | Williamson, IV |
| 5,366,134 A | 11/1994 | Green et al. |
| 5,389,102 A | 2/1995 | Green et al. |
| 5,392,979 A | 2/1995 | Green et al. |
| 5,398,861 A | 3/1995 | Green |
| D357,316 S | 4/1995 | Green et al. |
| 5,413,584 A | 5/1995 | Schulze |
| 5,415,334 A | 5/1995 | Williamson, IV et al. |
| 5,417,361 A | 5/1995 | Williamson, IV |
| 5,423,856 A | 6/1995 | Green |
| 5,456,401 A | 10/1995 | Green et al. |
| 5,478,003 A | 12/1995 | Green et al. |
| 5,480,089 A | 1/1996 | Blewett |
| 5,482,197 A | 1/1996 | Green et al. |
| 5,489,058 A | 2/1996 | Plyley et al. |
| 5,489,287 A * | 2/1996 | Green et al. ................ 606/139 |
| 5,505,363 A | 4/1996 | Green et al. |
| 5,509,596 A | 4/1996 | Green et al. |
| 5,514,149 A | 5/1996 | Green et al. |
| 5,542,594 A | 8/1996 | McKean et al. |
| 5,544,802 A | 8/1996 | Crainich |
| 5,549,619 A | 8/1996 | Peters et al. |
| 5,551,622 A | 9/1996 | Yoon |
| 5,558,266 A | 9/1996 | Green et al. |
| 5,562,241 A | 10/1996 | Knodel et al. |
| 5,571,285 A | 11/1996 | Chow et al. |
| 5,573,541 A | 11/1996 | Green et al. |
| 5,579,978 A | 12/1996 | Green et al. |

| | | |
|---|---|---|
| 5,584,859 A | 12/1996 | Brotz |
| 5,591,178 A | 1/1997 | Green et al. |
| 5,593,423 A | 1/1997 | Person et al. |
| 5,618,311 A | 4/1997 | Gryskiewicz |
| 5,645,567 A | 7/1997 | Crainich |
| 5,658,312 A | 8/1997 | Green et al. |
| 5,662,258 A | 9/1997 | Knodel et al. |
| 5,662,655 A | 9/1997 | Laboureau et al. |
| 5,667,527 A | 9/1997 | Cook |
| 5,706,997 A | 1/1998 | Green et al. |
| 5,725,538 A | 3/1998 | Green et al. |
| 5,728,108 A | 3/1998 | Griffiths et al. |
| 5,794,834 A | 8/1998 | Hamblin et al. |
| 5,816,471 A | 10/1998 | Plyley et al. |
| 5,829,662 A | 11/1998 | Allen et al. |
| 5,871,135 A | 2/1999 | Williamson IV et al. |
| 5,878,937 A | 3/1999 | Green et al. |
| 5,902,319 A | 5/1999 | Daley |
| 5,908,427 A | 6/1999 | McKean et al. |
| 5,947,999 A | 9/1999 | Groiso |
| 5,976,160 A | 11/1999 | Crainich |
| 5,984,949 A | 11/1999 | Levin |
| 5,993,476 A | 11/1999 | Groiso |
| 6,045,560 A | 4/2000 | McKean et al. |
| 6,083,242 A | 7/2000 | Cook |
| 6,090,131 A | 7/2000 | Daley |
| 6,120,526 A | 9/2000 | Daley |
| 6,131,789 A | 10/2000 | Schulze et al. |
| 6,149,658 A | 11/2000 | Gardiner et al. |
| 6,159,224 A | 12/2000 | Yoon |
| 6,241,747 B1 | 6/2001 | Ruff |
| 6,250,532 B1 | 6/2001 | Green et al. |
| 6,270,517 B1 | 8/2001 | Brotz |
| 6,387,104 B1 | 5/2002 | Pugsley et al. |
| 6,387,113 B1 | 5/2002 | Hawkins et al. |
| 6,409,743 B1 | 6/2002 | Fenton, Jr. |
| 6,423,088 B1 | 7/2002 | Fenton, Jr. |
| 6,599,310 B2 | 7/2003 | Leung et al. |
| 6,619,529 B2 | 9/2003 | Green et al. |
| 6,626,916 B1 | 9/2003 | Yeung et al. |
| 6,629,988 B2 | 10/2003 | Weadock |
| 6,638,297 B1 | 10/2003 | Huitema |
| 6,726,705 B2 | 4/2004 | Peterson et al. |
| 6,773,437 B2 | 8/2004 | Ogilvie et al. |
| 7,112,214 B2 | 9/2006 | Peterson et al. |
| D532,107 S | 11/2006 | Peterson et al. |
| 2002/0007184 A1 | 1/2002 | Ogilvie et al. |
| 2002/0019636 A1 | 2/2002 | Ogilvie et al. |
| 2002/0133181 A1 | 9/2002 | Tong |
| 2003/0236551 A1 | 12/2003 | Peterson et al. |
| 2004/0059377 A1 | 3/2004 | Peterson et al. |
| 2005/0149064 A1 | 7/2005 | Peterson et al. |
| 2005/0182444 A1 | 8/2005 | Peterson et al. |

OTHER PUBLICATIONS

Brochure: *La Sutura Perde il Filo*, Farmitalia Carlo Erba, 4 pgs., not dated.

*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-116, 1994.

\* cited by examiner

MECHANICAL METHOD AND APPARATUS FOR TISSUE FASTENING

RELATED APPLICATIONS AND PRIORITY CLAIM

The present application is a continuation application of U.S. patent application Ser. No. 10/448,838, filed May 30, 2003, entitled "Mechanical Method and Apparatus for Bilateral Tissue Fastening", which is a divisional of U.S. patent application Ser. No. 10/179,628, filed Jun. 25, 2002, now issued as U.S. Pat. No. 6,726,705, and is also a continuation-in-part application of U.S. Continuation-In-Part application Ser. No. 10/607,497, entitled "Mechanical Method and Apparatus for Bilateral Tissue Fastening", filed Jun. 25, 2003 and U.S. Continuation-In-Part application Ser. No. 10/603,397, entitled "Dynamic Bioabsorbable Fastener for Use in Wound Closure", filed Jun. 25, 2003 now U.S. Pat. No. 7,112,214, all of which are herein incorporated by reference in their entirety.

FIELD OF THE INVENTION

The present invention relates generally to the field of surgical instruments such as surgical staplers, clip applicators and sutureless closure devices. More particularly, the present invention relates to a mechanical method and apparatus for fastening tissue, such as skin tissue, with a fastener positioned below the tissue surface that secures opposed pieces of tissue.

BACKGROUND OF THE INVENTION

When an opening in tissue is created either through an intentional incision or an accidental wound or laceration, biological healing of the opening commences through the proximity of the opposed living tissue surfaces. If the opening is very large or if its location subjects the wound to continual movement, a physician will seek to forcibly hold the sides of the opening in close proximity so as to promote the healing process.

In the case of skin tissue, for example, healing occurs best when the opposing dermal layers of the skin tissue are held in proximity with each other. Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer is the bottom layer of skin tissue and includes less connective tissue making this the weakest layer of skin tissue.

The most prevalent method for forcibly closing a tissue opening is through the use of a suture or "stitches." As early as the second century, the Greeks were using sutures to physically close skin openings. In its simplest form, a suture is simply a length of material that is attached to a tissue-piercing device, such as a needle, and looped through the opposing sides of an opening. The suture is then pulled tight and the loop closes causing the opposing sides of the tissue to come into close physical proximity. The suture loop is held tight by the tying of a knot or some other locking mechanism. The first sutures were made of animal gut. Eventually other natural suture materials including leather, horsehair, flax, cotton and silk came into use.

As the sciences of medical and materials technology have advanced over the course of the past century, new bioabsorbable materials have been developed to further improve upon the basic suturing concept. Examples of modern improvements to the suturing process include enhancements to the suturing apparatus as shown, for example, in U.S. Pat. Nos. 755,921, 2,439,383, 2,959,172, 3,344,790 and 3,633,582, as well as advances in sutures and suture materials as shown, for example, in U.S. Pat. Nos. 3,123,077, 3,297,033, 3,636,956, 3,792,010 4,027,676 and 4,047,533. More recently, the suturing apparatus has been improved in the way of developing surgical "sewing machines" as shown, for example, in U.S. Pat. Nos. 5,496,334, 5,728,112, 5,735,862, 5,876,412, and 6,332,889, as well as in U.S. Publication Ser. Nos. 20030171761A1 and 20030216755A1. In addition, the suturing apparatus has been improved and tailored for specialty applications, for example endoscopic applications as shown, for example, in U.S. Pat. Nos. 5,080,663, 5,389,103, 5,522, 820, 5,578,044, 5,674,230, 5,797,927, 5,817,110, 5,871,488, 5,938,668, 5,976,161, and 6,641,592, as well as in U.S. Publication Ser. Nos. 20020049453A1, 20020065526A1, 0020128666A1, 20030105475A1, 20030105476A1, and 20030114863A1. Finally, suturing applications have been developed in which a secondary tissue fixation method is used in conjunction with a suture as shown, for example, in U.S. Pat. Nos. 6,264,675 and 6,478,809.

While suturing remains a popular method of effectuating closure of skin openings, the use of staples and staplers as a skin closure technique has become increasingly popular, especially in surgical settings where the opening is created through a purposeful incision. In these settings, the incision tends to make a clean, straight cut with the opposing sides of the incision having consistent and non-jagged surfaces. Typically, stapling of a skin opening, for example, is accomplished by manually approximating the opposing sides of the skin opening and then positioning the stapler so that a staple will span the opening. The stapler is then manipulated such that the staple is driven into the skin with one leg being driven into each side of the skin and the cross-member of the staple extending across the opening external to the skin surface. Generally, the legs of the staple are driven into an anvil causing the staple to deform so as to retain the skin tissue in a compressed manner within the staple. This process can be repeated along the length of the opening such that the entire incision is held closed during the healing process.

Much work has been devoted to improving upon the basic stapling process. Developments have gone in a variety of directions and include work devoted to the stapling apparatus as shown, for example, in U.S. Pat. Nos. 3,082,426, 3,643, 851, 4,410,125, 4,493,322, 4,592,498, 4,618,086, 4,776,506, 4,915,100, 5,044,540, 5,129,570, 5,285,944, 5,392,979, 5,489,058, 5,551,622, 5,662,258, 5,794,834, 5,816,471, 5,893,855, 6,131,789, 6,250,532 and 6,283,984. In addition to the stapling apparatus, developments have also been made in the staple design as shown, for example, in U.S. Pat. Nos. 2,351,608, 2,526,902, 2,881,762, 3,757,629, 4,014,492, 4,261,244, 4,317,451, 4,407,286, 4,428,376, 4,485,816, 4,505,273, 4,526,174, 4,570,623, 4,719,917, 4,741,337, 5,007,921, 5,158,567, 5,258,009, 5,297,714, 5,324,307, 5,413,584, 5,505,363 and 5,571,285.

In some instances, work has been devoted to combining the advantages of sutures and staples into a single medical fastener for purposes of wound closure. Various different styles and techniques of combining sutures and staples have evolved as shown, for example, in U.S. Pat. Nos. 5,342,376, 5,425, 747, 5,584,859, 5,931,855, 6,106,544, 6,270,517, and 6,599, 310.

While modern suturing and stapling techniques continue to provide an effective manner of effectuating skin closure, there remains a series of inherent disadvantages in using either of these techniques. The standard technique for both suturing and stapling includes puncturing both the epidermis and dermis. This can result in a wound closure having an unaesthetically pleasing appearance on the surface of the skin. The presence of the fastener exposed through the skin surface provides an opportunity for infection and for accidentally catching the fastener and tearing the wound open. In the case of non-absorbable fasteners, further action by a medical professional is necessary in order to remove the fastener once biological healing is complete.

In order to overcome these limitations, practitioners have developed a number of specialized suturing techniques where the suture is passed only through the dermis effectively positioning the suture below the skin surface, or in a subcuticular fashion. A surgeon has the choice of placing individual or interrupted sutures along the length of an opening. Another suturing option is for the surgeon to use a single strand of suture material to place a plurality of continuing suture loops or running sutures along the length of an opening. While the presence of the suture below the surface can improve the aesthetic nature of the closure, it requires greater skill and technique to accomplish effectively and takes longer than conventional external suturing.

While there has been active development of dermal layer suturing techniques, little has been done in the area of staples and staplers for use in connection with the dermal layer. In a series of patents issued to Green et al., including U.S. Pat. Nos. 5,292,326, 5,389,102, 5,489,287 and 5,573,541, a subcuticular stapling method and apparatus are disclosed that were ultimately commercialized as the U.S. Surgical SQS Subcuticular Stapling Apparatus. The Green et al. patents describe a stapling technique employing a handheld apparatus with jaws to proximate, interdigitate and overlap opposing sides of dermal layer tissue along the length of a skin opening. The apparatus then drives a single spike through the interdigitated and overlapped dermal layers of the opposing skin surfaces in order to secure both sides of the dermal tissue on the single spike. Although this technique reduced the time required to effectuate a subcuticular skin closure, the SQS device was not commercially successful in part because the resulting closure produced an undesirable wave-like scar that sometimes did not heal effectively.

Another alternative bioabsorbable approach is disclosed and described in a series of patents issued to Brotz, including U.S. Pat. Nos. 5,425,747, 5,584,859, 6,270,517 and 6,478,809. The Brotz patents describe a suturing technique using a bioabsorbable suture structure having a plurality of lateral members extending perpendicularly from a central body member. Lateral members on opposed sides of the central body extend into tissue on opposing sides of an incision whereby the lateral members hold the incision closed.

Another bioabsorbable approach for wound closure is disclosed and described in U.S. Pat. No. 6,645,226 that comprises a series of attachment points projecting from a common supportive backing. The backing is then placed below the wound, generally in the sub-dermal layer, such that the backing extends across the wound. Next, the tissue is pressed over the attachment points such that the wound stress is distributed by the backing.

In yet another bioabsorbable approach for wound closure, U.S. Pat. No. 6,599,310 to Leung et al., describes a barbed suture that can be used for approximating and retaining subcuticlar tissue during the healing process. The barbed suture can be looped by a surgeon through opposing sides of a tissue wound, along the length of the wound, whereby the suture is pulled tight and the wound is held closed.

Unfortunately, none of these bioabsorbable fasteners designed for use in the dermal layer have achieved significant commercial or medical success.

A novel bilateral approach to fastening dermal tissue using bioabsorbable fasteners is disclosed and described in U.S. Pat. No. 6,726,705, as well as in U.S. patent application Ser. Nos. 10/448,838, 10/607,497 and 10/603,397, to Peterson et al, all of which are commonly assigned to the assignee of the present application and all of which are incorporated by reference in their entirety. This bilateral approach to tissue fastening first manipulates opposed sides of tissue to form target tissue zones followed by a bilateral insertion of a tissue fastener to retain opposed dermal layers across an incision or wound in close approximation to facilitate healing. By maintaining contact of the dermal layers through the healing process, the healing process is enhanced which results in less chance of infection, faster recovery and improved aesthetic appearance. In addition, no subsequent medical follow-up is necessary to remove fasteners as is typically necessary with nonabsorbable fasteners.

While the bilateral tissue fastening methods and apparatus taught by Peterson et al. provide many advantages, it would be advantageous to extend the principles taught by Peterson et al. to other suitable tissue fastening applications.

SUMMARY OF THE INVENTION

The present invention is a mechanical system for unilaterally securing opposing sides of skin tissue in a sequential or alternating manner. A tissue manipulator is used to retain a portion of an interior surface of each of two pieces of living dermis tissue along a vertical interface below an exterior surface in order to present a target tissue zone for each piece of tissue. An applicator apparatus includes a driving head portion and a handle portion positioned at least partially above the exterior surface. The applicator apparatus unilaterally drives at least one portion of a fastener first through one target tissue zone and then through the target tissue zone of the other piece of dermis tissue. The two pieces of dermis tissue can be brought together before, during or after the insertion of the fastener.

In one embodiment, a fastener is driven sequentially through a pair of target tissue zones defined on opposing sides of a tissue interface. The pair of target tissue zones may be located directly across the tissue interface from one another or may be displaced such that one target tissue zone is forward of the other target tissue zone relative to the tissue interface. The fastener can have has flexible body portion with a barb at a distal end. The fastener can further comprise an attachment flap at a proximal end. The attachment flap can include a slot formed therethrough, which is adapted to receive the barb. The applicator assembly can include an anvil portion with a concave deflector. The concave deflector causes the flexible body portion to bend and advance from one target tissue zone, across the tissue interface and into the other target tissue zone. Once the barb emerges from the second target tissue zone, the attachment flap may be bent so that barb can be captured such that the secured fastener forms a loop capturing both sides of the skin opening. In an alternative embodiment, the application assembly can make use of a single U-shaped needle in place of a pair of generally parallel pilot needles. Numerous other combinations of sequential, unilateral fastener insertion and tissue capture are contemplated by the scope of the present invention.

DETAILED DESCRIPTION OF THE PREFERRED EMBODIMENTS

Figure 1:
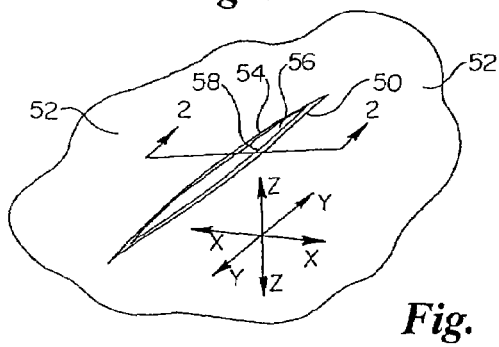
FIG. 1 shows a typical opening in skin tissue such as may be closed by the present invention.
Figure 2:
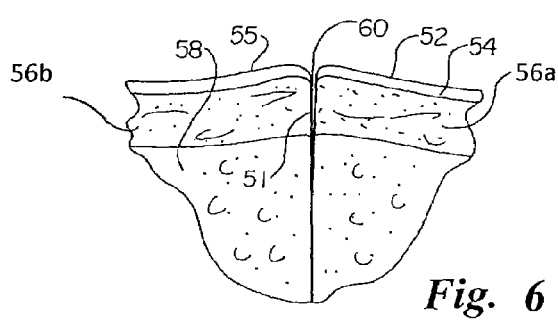
FIG. 2 shows a cross-sectional view of the skin tissue and opening of FIG. 1.
Figure 3:
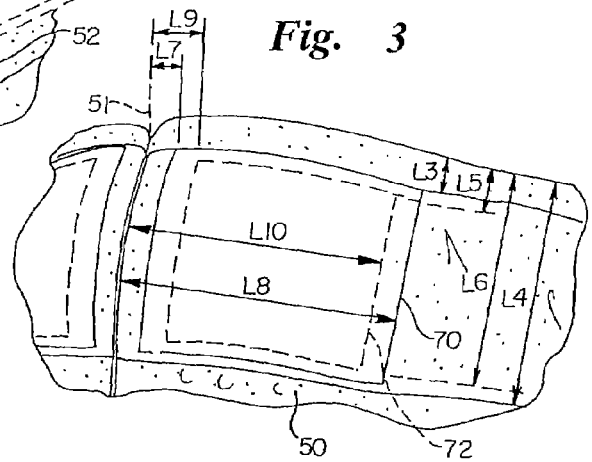
FIG. 3 shows an enlarged view of a target tissue zone.

In FIGS. 1-3 there is shown a depiction of a typical opening 50 in the surface of skin 52, such as may be made, for example, by a surgical incision or a wound. As illustrated in FIG. 1, for purposes of describing the present invention, opening 50 may be described as having a length or longitudinal orientation parallel to the y-y axis, a width orientation parallel to the x-x axis, and a depth orientation parallel to the z-z axis. The x-y-z axis for purposes of the present invention is defined with respect to an external tissue surface, which in the case of skin 52 is the outer surface. References to a vertical and horizontal planar orientation in connection with the present invention are made with respect to the external tissue surface at the site of the opening in question. The vertical inner surfaces 60 formed by each side of the opening 50 can be visualized as meeting along a generally vertical interface 51. It will be understood that in the case of an opening that extends over a curved tissue surface, the corresponding horizontal and vertical surfaces associated with the opening will be defined with respect to such curved tissue surface. It also will be understood that the vertical interface 51 may be vertical in only one orientation with respect to the tissue surface, such as in the case when an angled incision has formed the opening 50.

As is best illustrated in the sectional views of FIGS. 2 and 3, human skin 52 generally has three discrete layers. These layers comprise an epidermal layer 54 of mostly non-living tissue having an exterior surface 55, a dermal layer 56 of mostly living tissue, and a subcutaneous tissue layer 58. Although the preferred embodiment of the present invention will be described with respect to human skin tissue 52, it will be understood that the present invention is applicable to closure of openings in other types of tissue having generally defined surfaces, such as fascia, membranes organs, vessels, vasculature, vascular pedicles, skin grafts, bladder and other biocompatible materials with generally defined surfaces such as artificial skin, artificial membranes and synthetic mesh.

Figure 4:
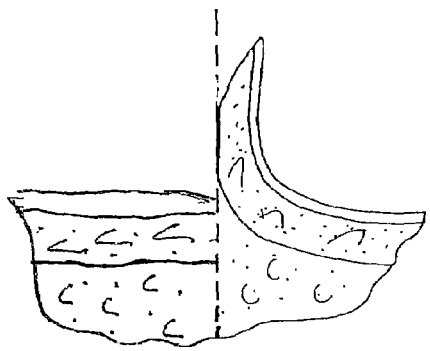
FIG. 4 shows a cross-section view of unilaterally everted skin tissue.
Figure 6:
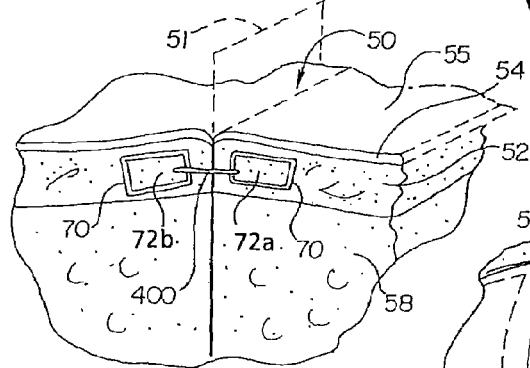
FIG. 6 shows a cross-section view of a wound having a fastener sequentially inserted through opposed target tissue zones.

It has long been known that the most rapid healing of a skin opening with a minimum of scarring occurs when the inner surfaces 60 of the living dermal layer 56 at each side of the vertical interface 51 of skin opening 50 are brought together and held in close contact as illustrated in FIG. 6. One method of approximating the inner surfaces 60 is by everting the dermal layers 56. One method of everting the dermal layers 56 is through simultaneous bilateral capture of the dermal layers 56 as disclosed and describe in the related U.S. Pat. No. 6,726,705 and U.S. patent application Ser. Nos. 10/179,628, 10/607,497, and 10/603,397. Alternatively, the dermal layers 56 can be unilaterally and sequentially everted, for example, as shown in FIGS. 4 and 5.

Figure 7:
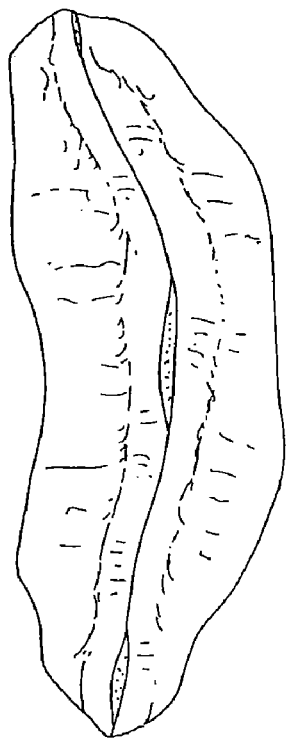
FIG. 7 is a pictorial representation of a skin opening closed with conventional subcutaneous sutures.
Figure 8:
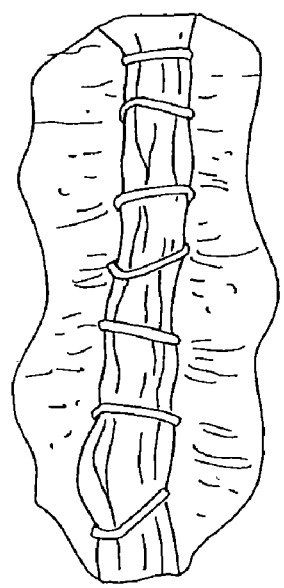
FIG. 8 is a pictorial representation of a skin opening closed by conventional surgical stapling.
Figure 9:
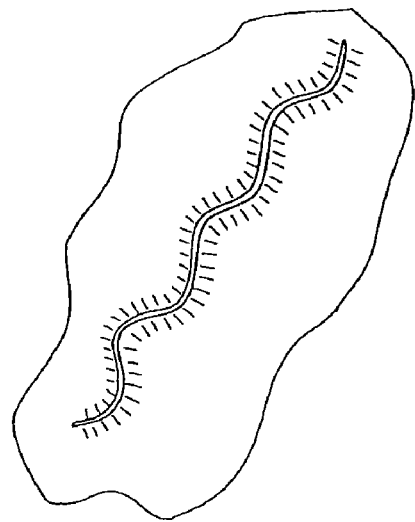
FIG. 9 is a pictorial representation of an opening closed with the prior art interdigitated subcuticular stapler.

The ability of the present invention to provide a more effective and efficacious tissue closure can be seen with reference to FIGS. 7, 8, 9 and 10, which show skin openings closed by various prior art methods as compared with an opening closed using the bilateral fastening techniques of the present invention. In FIG. 7, there is shown a skin opening closed with subcutaneous sutures. The generally everted condition of the closed opening can produce unattractive scarring and less than optimal healing if the eversion is excessive or inadequate. As can be seen from FIG. 7, obtaining consistency from suture to suture is difficult and the quality of the closure is highly dependent upon the skill of the surgeon. FIG. 8 shows a skin opening closed by conventional surgical stapling. In addition to the generally unattractive appearance of the closed opening, staple openings and the excessive everted condition of the opening may lead to undesirable scarring. In addition, if non-resorbable staples are used, the staples must be removed before complete healing can occur. FIG. 9 shows a depiction of an opening closed with the interdigitated subcuticular stapler known as the SQS device that is described, for example, in U.S. Pat. Nos. 5,292,326, 5,389,102, 5,489, 287 and 5,573,541. The characteristic undulating appearance caused by the overlapping interdigitation of the skin may lead to an unusual appearing scar in the healed opening. The overlapping and interdigitation of the skin can also cause epidermis tissue to be interposed between dermal layers, thereby leading to incomplete healing or excessive scarring.

Figure 10:
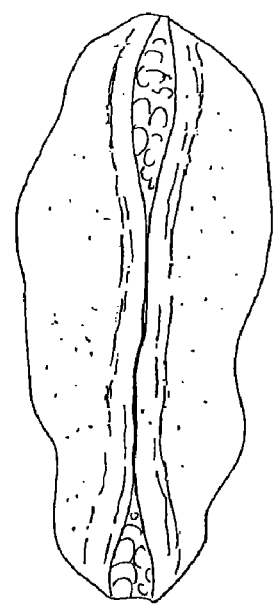
FIG. 10 is a pictorial representation of an opening closed using the bilateral fastening technique of the present invention.

By comparison, an opening that has been partially closed by the method and using the apparatus of the present invention is shown in FIG. 10. As shown, the closed portion of the opening is tightly closed, yet lies flat without undue eversion of the opening leading to better healing performance with minimal scarring. There is consistency in the closure from fastener to fastener. Because the fasteners are positioned below the skin surface (i.e., subcuticular), the fasteners are not exposed and there is no puncturing or button holing of the epidermis that can lead to the increased possibility of infection or interference with the normal healing process. In addition, if fasteners made of a bioresorbable, bioabsorbable or even a bioerodible material are used, there is no need to later remove the fasteners.

Figure 5:
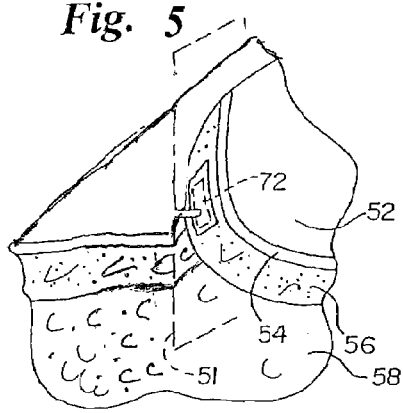
FIG. 5 shows a cross-section view of unilaterally everted skin tissue including a unilaterally inserted fastener.

The advantages of the present invention are accomplished by an apparatus and method that unilaterally engages target tissue zones 70, shown in FIGS. 3, 5 and 6, on each side of a skin opening 50 with a fastener that is preferably made of a bioresorbable material. As used in connection with the present invention, the term unilaterally refers to a single axis of insertion for a fastener on one side of the vertical interface 51 of an opening 50. The unilateral engagement is then made on an opposed side of the vertical interface 51 such that a fastener is inserted sequentially through both target tissue zones 70. The fastener used may have a variety of configurations and be oriented in a variety of ways as will be further described herein. The location, geometry and orientation of the fastener and the dermal layers in relation to the mechanical apparatus of the present invention are all important considerations to obtaining the most optimal contact and compression of the dermal layer for efficacious closing of the opening. While the skin opening 50 will be described in connection with an opening in a single piece of tissue, it will be understood that the opening 50 could also be between two separate and otherwise unconnected pieces of tissue, or even between a piece of tissue and a piece of biocompatible material to be secured to that piece of tissue.

As is shown in FIGS. 3, 5 and 6, there exists an optimal target tissue zone 70 on each side of vertical interface 51 that may be bilaterally engaged by a fastener in order to achieve optimal dermal contact for healing. This target tissue zone 70 lies within the dermal layer 56, and can be visualized as a rectangular cross-sectional area when the tissue is in a relaxed condition as shown best in FIG. 3. In addition, within target tissue zone 70, there exists a most preferred area 72 for tissue engagement. In the depth orientation, target tissue zone 70 lays between a distance L3 of about 0.1 mm below the surface 55 of epidermal layer 54, and a distance L4 up to 2.0 mm below the surface 55. The most preferred area 72 lies between a distance L5 of about 0.2 mm and a distance L6 of about 0.8 mm below the surface. In the width orientation, target tissue zone 70 lies between a distance L7 of about 1.0 mm and a distance L8 of about 20.0 mm from vertical interface 51. Most preferred area 72 lies between a distance L9 of about 2.0 mm and a distance L10 of about 8.0 mm from vertical interface 51. Because the target tissue zone 70 is not visible to an operator, the manipulator assembly 400 and applicator assembly 100 are preferably designed to consistently and repeatedly enable the operator to position the target tissue zone 70 for deployment of a fastener 400.

As illustrated in FIG. 5, due to the inherent flexibility and resilience of skin tissue, it is most desirable that a fastener 400 be deployed into the target tissue zone 70 while the skin opening is everted. A first dermal layer 56a is everted, as shown in FIG. 4, followed by the insertion of fastener 400 into a first target tissue zone 72a as shown in FIG. 5. The process is then repeated such that a second dermal layer 56b is everted followed by the sequential insertion of the fastener 400 into a second target tissue zone 72b. Once the eversion and insertion is accomplished on both sides of opening 50, fastener 400 retains the first dermal layer 56a and second dermal layer 56b in proximity during the healing process as illustrated in FIG. 6. To the extent that the primarily non-living material of epidermal layer 54 can be excluded from the healing opening, the rapidity and level of scar tissue formed during the healing process will be improved. The dermal layers 56 are retained in close contact with each other by the fastener 400 after the everting pressure is removed and the skin relaxes into a flat condition as shown in FIG. 6.

Figure 11:
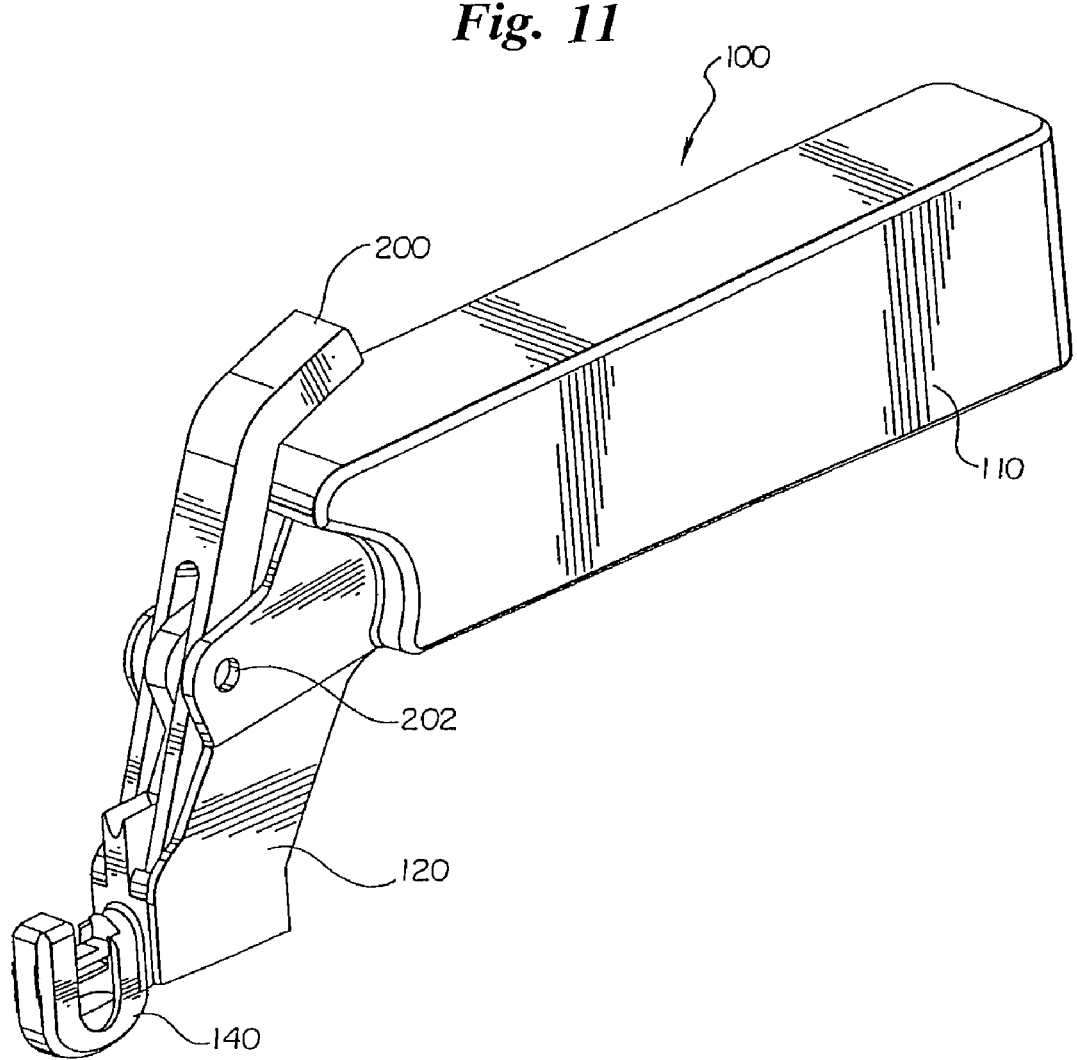
FIG. 11 is a perspective view of an embodiment of an applicator apparatus of the present invention.

An embodiment of an applicator assembly 100 of the present invention is shown in FIG. 11. The application assembly 100 generally comprises upper handle portion 110 and lower handle portion 120, to which is attached driving head 140. Trigger 200, which pivots about pivot 202 is provided to allow user actuation of the mechanism. Although a manual pivoting trigger arrangement 200 is shown, it will be understood that a variety of other user-actuated manual triggers, buttons or actuator mechanisms may be utilized with the applicator assembly 100, such as a push button, slide mechanism, cam mechanism, spring actuated apparatus, cable actuated pull mechanism, rotating mechanism or tab actuated trigger. Alternatively, an automatic actuator in the form of an electronic, pneumatic, motion controlled, remote controlled or computer-activated trigger may be used to operate the applicator 100.

Figure 12:
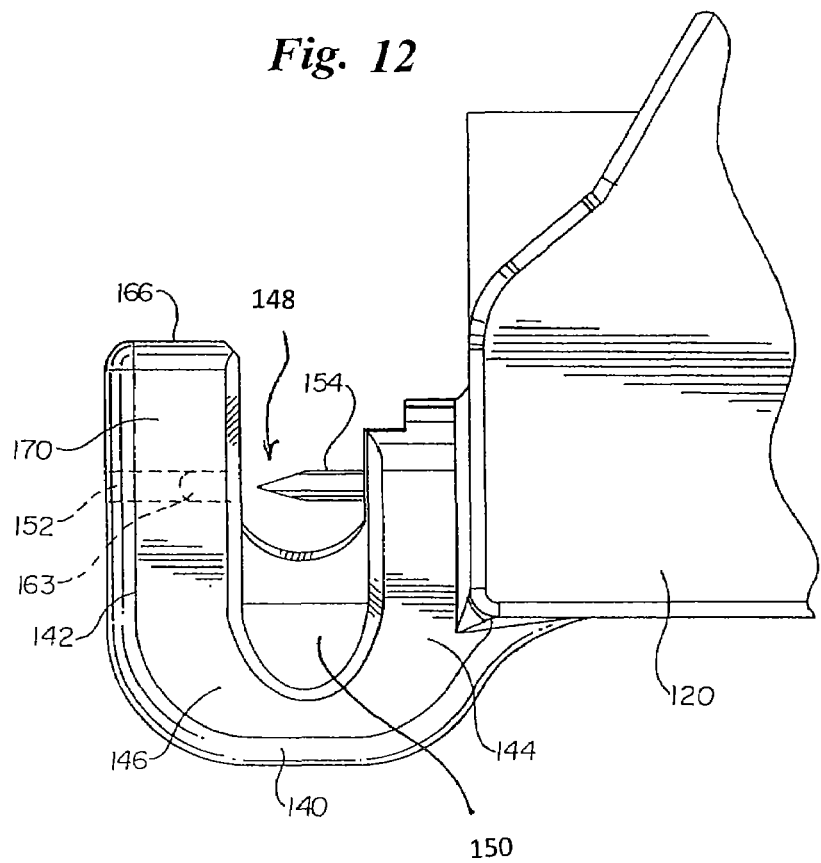
FIG. 12 is a side view of an insertion head of the present invention.
Figure 13:
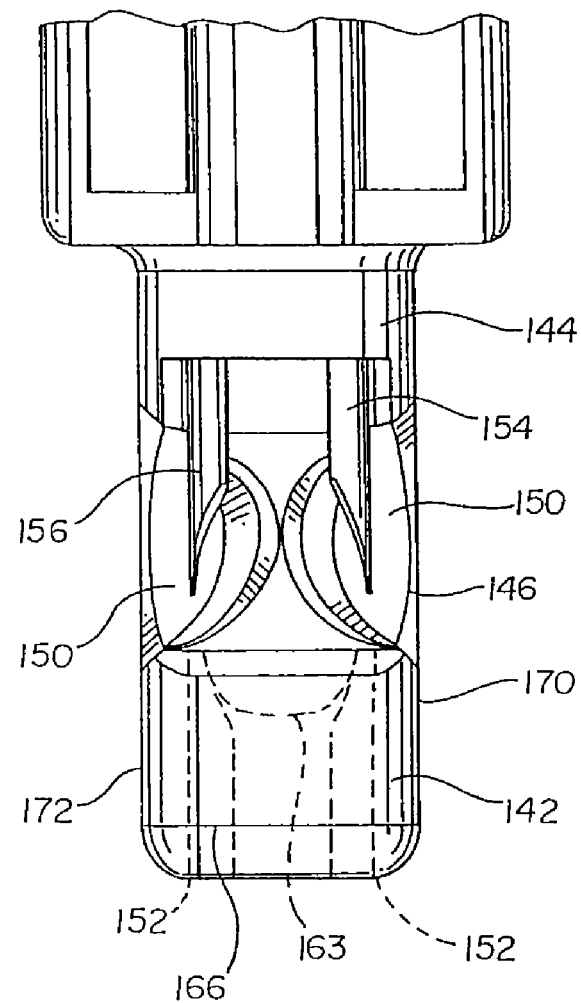
FIG. 13 is a plan view of the insertion head of FIG. 12.
Figure 14:
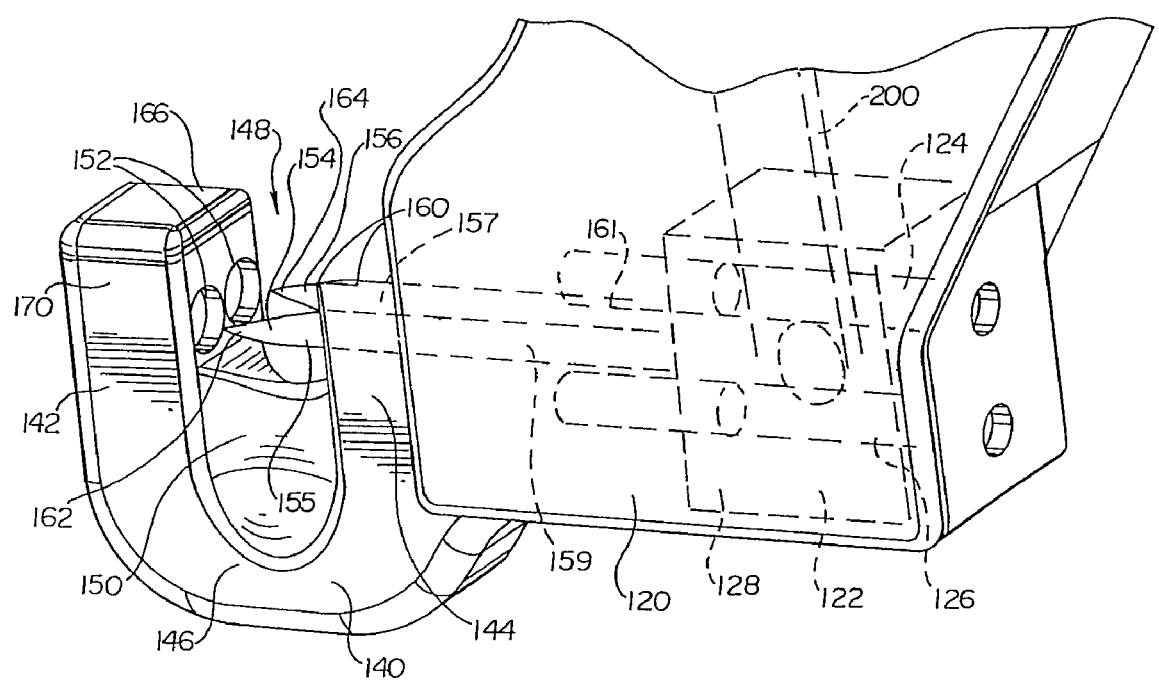
FIG. 14 is a perspective view of the insertion head of FIG. 12.
Figure 15:
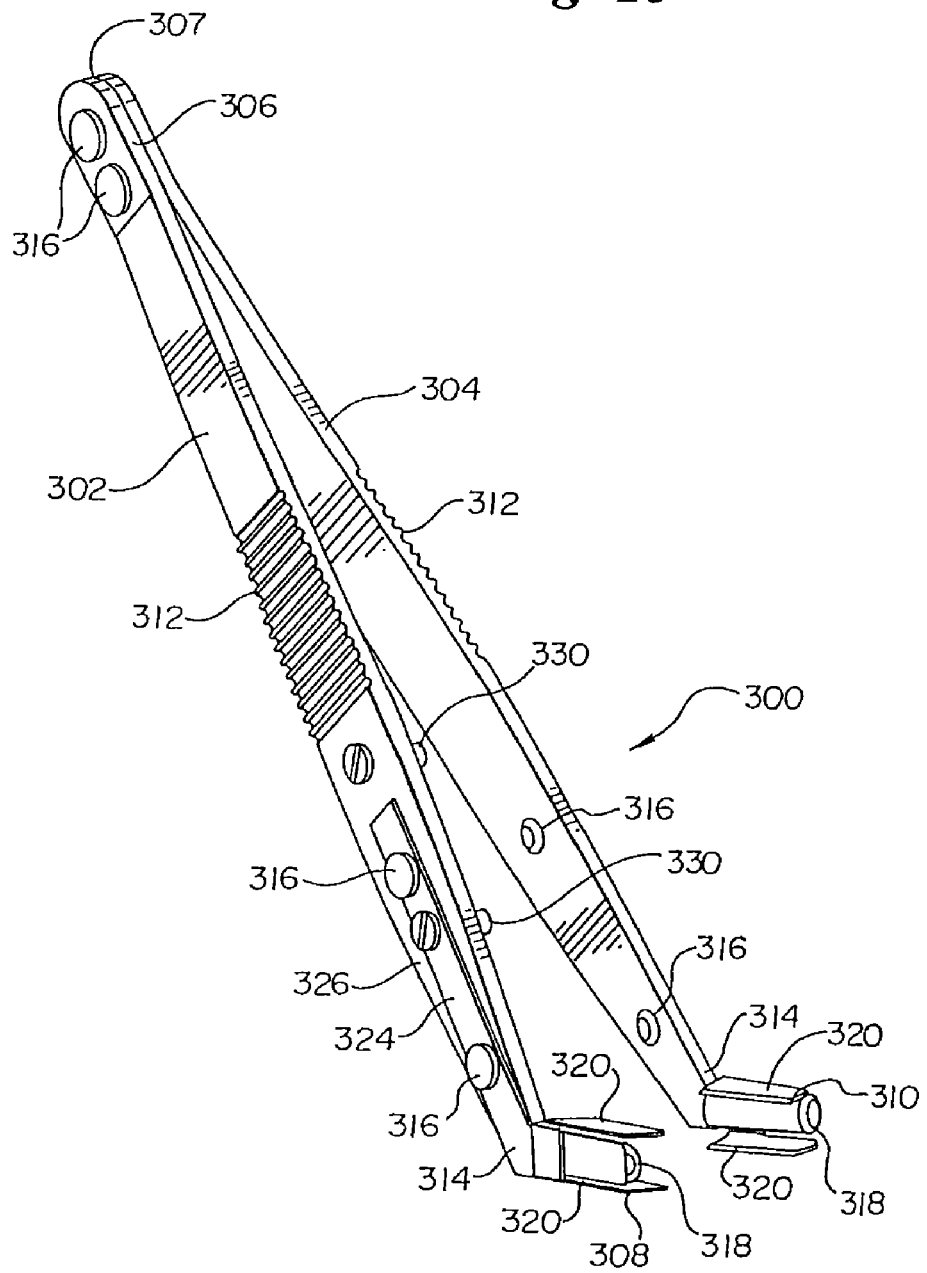
FIG. 15 is a perspective view of an embodiment of a tissue manipulator assembly.
Figure 16:
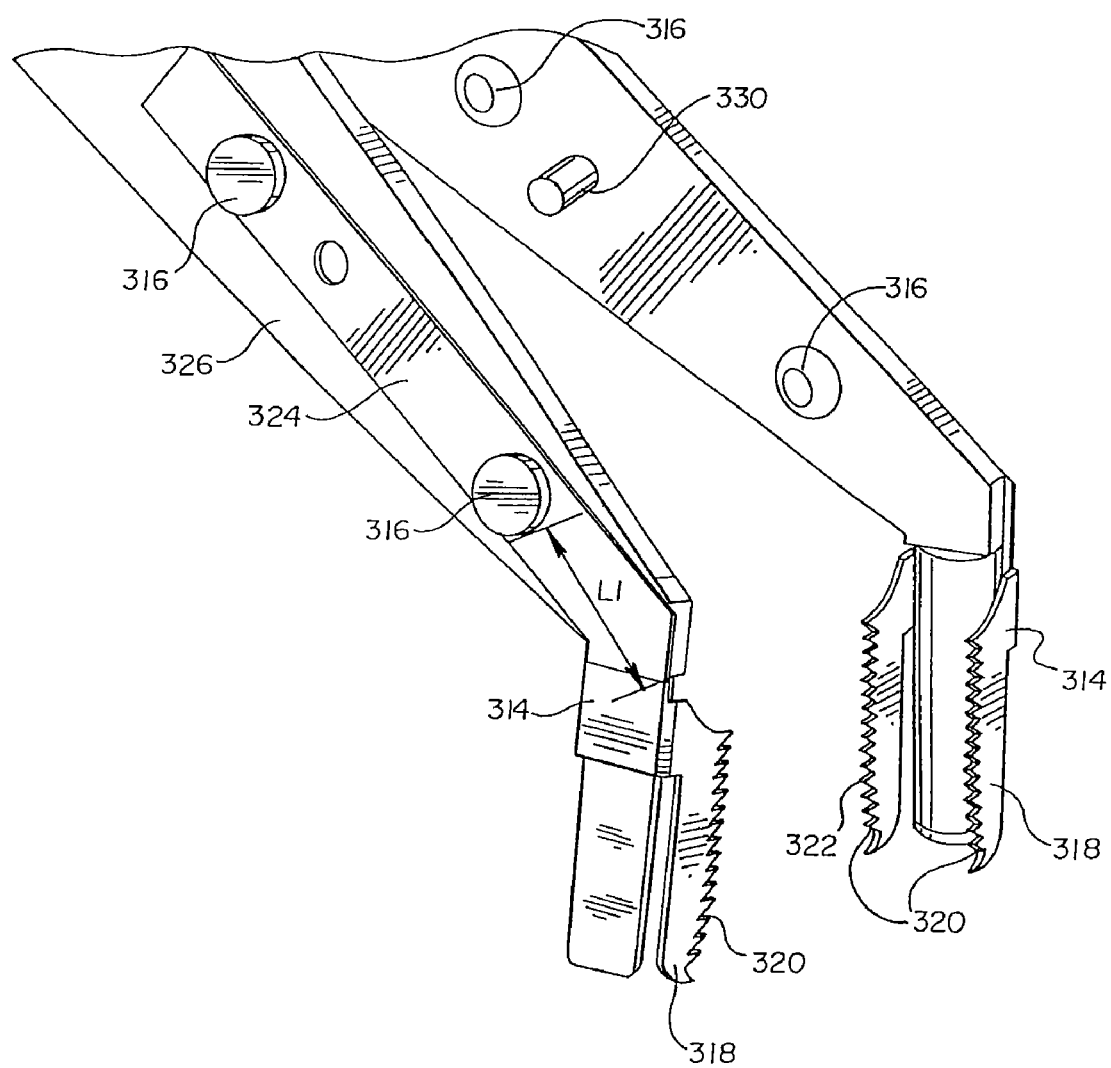
FIG. 16 is a perspective view of a pair of tissue forms on the tissue manipulator assembly of FIG. 15.
Figure 20:
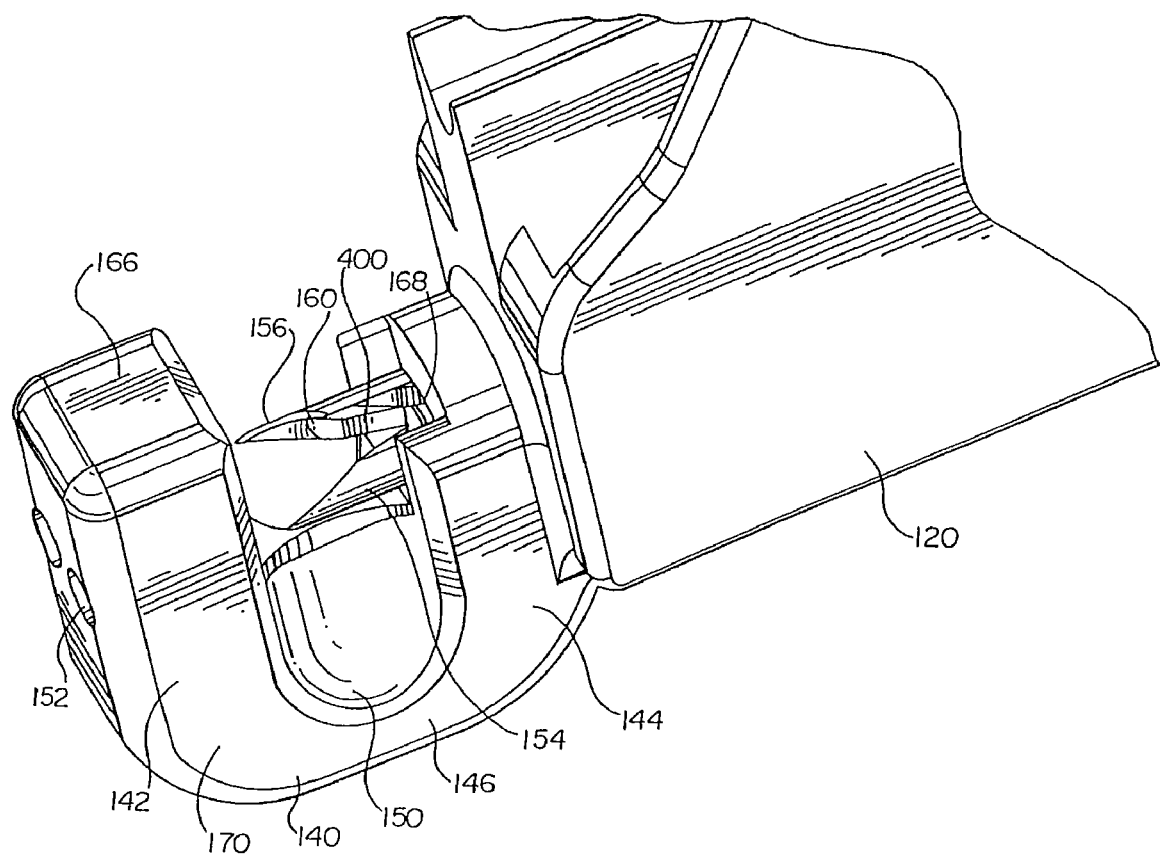
FIG. 20 is a perspective view of the insertion head of FIG. 12 inserting the sequential fastener of FIG. 17.
Figure 21:
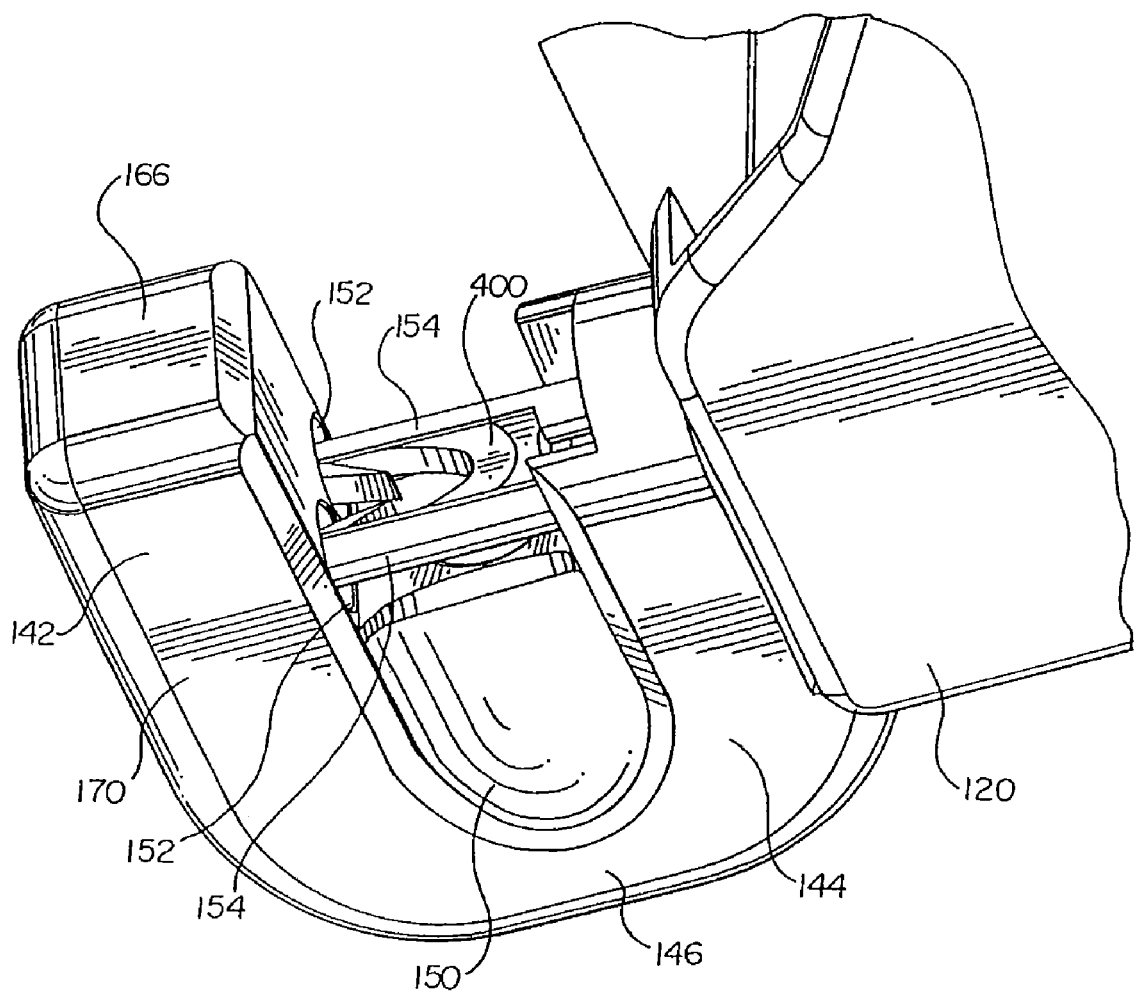
FIG. 21 is a perspective view of the insertion head of FIG. 12 inserting the sequential fastener of FIG. 17.

In FIGS. 12-14, there are shown detailed views of an embodiment of a driving head 140 and lower handle portion 120. Driving head 140 is preferably U-shaped and has an anvil portion 142 separated from backing portion 144 by a cross-member 146, thereby forming a gap 148. Cross-member 146 preferably has concave areas 150 allowing the dermal layer 56 of skin to be compressed into gap 148 such that target tissue zones 70 are presented for capture on either side of vertical interface 51 as will be further explained hereinbelow. Although driving head 140 is shown in a fixed orientation relative to lower handle portion 120 and upper handle portion 110, it will be understood that driving head 140 may be articulated, either in the plane of the vertical interface 51 or perpendicular to the plane of the vertical interface 51, to allow for increased maneuverability and orientation of driving head 140. Alternatively, lower handle portion 120 may be articulated relative to upper handle portion 110, or both lower handle portion 120 and driving head 140 may be articulated.

Preferably, anvil portion 144 of driving head 140 has apertures 152. Apertures 152 are appropriately sized so as to slidingly receive penetrators or pilot needles 154, 156 and may be bored directly into the material of anvil portion 144 or may be lined with a metal guide tube or the like inserted into a bore in anvil portion 144. Pilot needles 154, 156 have a generally arcuate shaped cross-section throughout distal portions 155, 157, and a solid cylindrical cross-section in proximal portions 159, 161. Each distal portion 155, 157 has an inner concave surface 158, 160 for accommodating and retaining a fastener 400, and proximal portion 159, 161 can engage the back surface of the fastener 400, allowing the fastener to be advanced distally with the needles. The distal ends 162, 164 of pilot needles 154, 156 can have a sharp point for penetrating skin. Alternatively, the distal ends 162, 164 can be configured merely for directing fastener 400 when the fastener 400 includes its own penetrating tip. Pilot needles 154, 156 are vertically disposed at a distance d1 below top surface 166 of anvil portion 142. It is preferably that top surface 166 be usable as a reference datum for visually gauging whether pilot needles 154, 156 are located within target tissue zone 70. Accordingly, it is preferable that distance d1 be between 0.1 mm and 2.0 mm, and most preferably between 0.2 mm and 0.8 mm, so that when top surface 166 is aligned with the outer skin surface, pilot needles 154, 156 are located within target tissue zone 70 and most preferably within most preferred area 72.

Delivery mechanism 128 serves to eject a fastener from driving head 140. Preferably, slide block 122 is slidably mounted on guides 124, 126, within lower handle portion 120. Slide block 122 is engaged with trigger 200 so that actuation of the trigger causes sliding movement of slide block 122. Pilot needles 154, 156 are fixedly attached to slide block 122, and extend outwardly through backing portion 144 of driving head 140 through slot 168. Thus, back and forth sliding motion of slide block 122 causes pilot needles 154, 156 to be extended and retracted from slot 168, gap 148 and apertures 152. It will be understood that any number of mechanical driving arrangements can be used to impart the necessary force to pilot needles 154, 156, or alternatively to the fastener 400 directly. Examples include sliding mechanisms, cam mechanisms, spring-operated mechanisms, screw drives, pneumatic drives, automated motion control drives, or the like.

Pilot needles 154, 156 are preferably spaced apart by an interneedle distance of between about 2.0 mm and 20 mm and most preferably between about 4.0 mm and 16.0 mm, so that when the driving head in placed within a skin opening to be fastened, and with the skin opening aligned with the approximate midpoint between the pilot needles, the pilot needles will be located within the width orientation of the target tissue zone 70.

Figure 17:
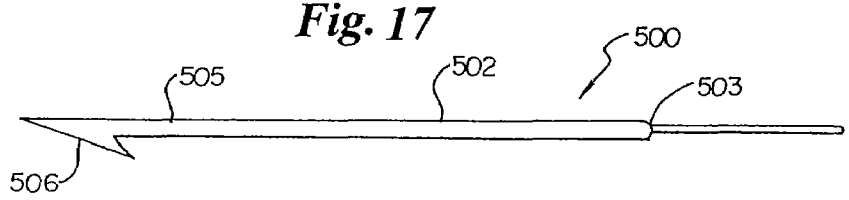
FIG. 17 is a side view of a sequential fastener of the present invention.
Figure 18:
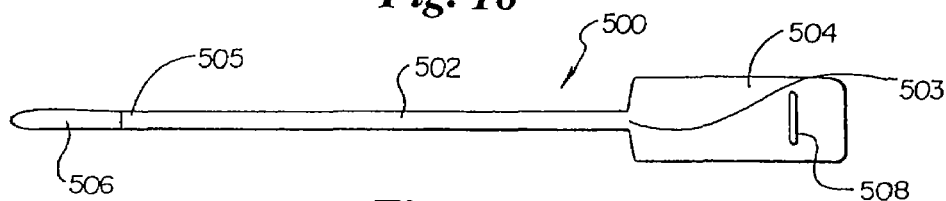
FIG. 18 is a plan view of the sequential fastener of FIG. 17.

In FIGS. 17 and 18, there is shown an embodiment of a tissue manipulator assembly 300 for use in approximating and everting tissue with respect to applicator assembly 100. The proximal ends 307 of arms 302, 304 are joined together at fulcrum 306, forming the tweezer-like structure of the overall assembly. Gripping areas 312 are provided on each arm to allow gripping of the assembly with the fingers. Any suitable fastening method may be used at fulcrum 306, including rivets 316 as shown, or the arms 302, 304 may be welded, cast, or molded together or may otherwise be integrally formed together. The material and overall dimensions for arms 302, 304 are selected so as to allow the arms to be resiliently compressed inwardly with the fingers, and with a memory characteristic for returning to the original position upon the removal of pressure. In addition, the material used for the arms and other portions of the assembly are preferably thermally and chemically stable so as to allow sterilization with either heat or chemical means. The preferred material for arms 302, 304 is stainless steel.

At the distal ends 309 of each arm 302, 304 are formed tissue manipulator surfaces 318. Manipulator surfaces 318 are preferably semi-cylindrically shaped as shown, with the diametrical dimension of each semi-cylinder selected so as to conform to the diameter and shape of the concave areas 150 of applicator assembly 100. Skin gripping jaw members 314 are preferably attached to the exterior surfaces 326 of each arm member 302, 304. Each jaw member 314 has a backing portion 324 for attaching to the arms, and a pair of inwardly directed projections 320 disposed on both sides of manipulator surfaces 318. Directly opposed serrations 322 are preferably provided on the inward-most edge of each projection 320 for better skin purchase. Backing member 324 may be attached to each arm 302, 304 using any suitable attachment method, including mechanical fasteners such as the rivets 316 as shown. For reasons that will be further explained, it is preferable that each jaw member 314 is of sufficient resilience and is attached so that inwardly directed projections 320 may deflect separately from skin manipulator surfaces 318 under moderate finger pressure applied to arms 302, 304. This may be achieved through concerted selection of the material used for jaw member 314, the thickness dimension of backing member 324, and the free length L1 of each backing member 324 between the inwardly directed projections 320 and the fastener 316 closest to the distal end 309 of the arm. The objective of the design of the backing member 324 is to have the jaw members 314 engage tissue with a first force and have the manipulator surfaces 318 engage tissue between the jaw members 314 with a second force that is greater than the first force. In addition, the use of a pair of directed projections 320 on each side of the vertical interface 51 serves to stabilize the tissue laterally between the pair of projections 320.

Mechanical stops 330 are provided to prevent pressure beyond that necessary to ensure optimal approximation of tissue into gap 148 and concave portions 150 of applicator assembly 100 from being transmitted through manipulator surfaces 318. Preferably, mechanical stops 330 are set so that manipulator surfaces 318 close to a distance that is spaced apart from the interneedle distance of pilot needles 154, 156 by a range of 0.2-0.8 millimeters, such that the total distance between mechanical stops 330 is 0.4-1.6 millimeters greater than the interneedle distance between pilot needles 154, 156. In a preferred embodiment in which the interneedle distance is set at 3.25 millimeter, the mechanical stops 330 would allow the surfaces 318 to close to within a range of 3.65-4.85 millimeters when approximating tissue into gap 148. Although jaw members 314 may be formed from any suitable material, the preferable material is stainless steel.

Figure 19:
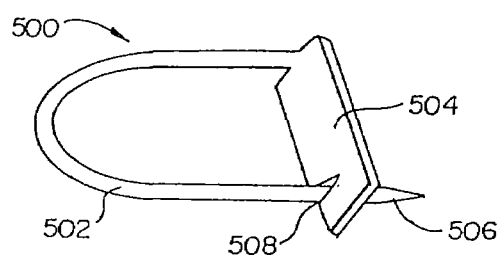
FIG. 19 is a perspective view of the sequential fastener of FIG. 17.

An embodiment of the fastener 500 for use in unilateral tissue capture and sequential fastener insertion is shown in FIGS. 17, 18 and 19. Fastener 500 has flexible body portion 502 with a barb 506 at distal end 505 and an attachment flap 504 at proximal end 503. Flexible body portion 502 is dimensioned so as to be received within either concave inner surface 158, 160 of pilot needles 154, 156. Attachment flap 504 has slot 508 formed therethrough, which is adapted to receive barb 506.

Fastener 500 can be applied using applicator assembly 100. In applicator assembly 100, anvil portion 142 has concave deflector 153 formed between apertures 152 and extending into a portion of each aperture 152 so that only an area of each aperture is open sufficient to allow the arcuate cross-section of pilot needles 154, 156 to pass. In operation, and with reference to FIGS. 1-6 and 11-19, fastener 500 is axially aligned with pilot needle 154, and is inserted within the corresponding concave inner surface of the needle with barb 506 oriented toward the point of the needle. Applicator assembly 100 is then introduced into the interface portion 51 of the skin opening 50 as described above. Tissue manipulator assembly 300 is then applied as before to bring the dermal layer 56 into contact within gap 148, and thereby properly positioning target tissue zone 70. As slide block 122 and the attached pilot needles 154, 156 are moved distally through actuation of trigger 280, fastener 500 is advanced through the skin tissue on one side of skin opening 50 along with pilot needle 154 in which it is disposed. Once the tip of barb 506 reaches aperture 152, however, it is engaged by, and begins to slide laterally along, concave deflector 163, causing flexible body portion 502 to bend. As pilot needles 154, 156 are further advanced, barb 506 is turned in direction 180 degrees by deflector 163. It will be appreciated that the barb 506 may either be positioned in front of pilot needle 154 by an amount sufficient to redirect barb 506 into the opposite direction or pilot needle 154 may advance into the corresponding aperture 152 to a depth at which the redirection of barb 506 upon the entry to aperture 152 will be sufficient to redirect barb 506 into the opposite direction. Once redirected and positioned in line with the second skive, barb 506 is advanced in the opposite direction by pilot needle 156 and through the skin tissue on the opposite side of the vertical interface 51 as pilot needle 156 is withdrawn. Once barb 506 emerges from the dermal tissue, attachment flap 504 may be bent so that barb 506 may be pushed through slot 508, thus securing fastener 500 in a loop and bilaterally capturing both sides of the skin opening 50. It will also be appreciated that attachment flap 504 may be replaced by suitable structure on flexible body 502 for engaging a suture. The suture lock of co-pending application entitled "Suture Lock Having Non-Through Bore Capture Zone," U.S. patent application Ser. No. 10/166,161, filed Jun. 10, 2002, which is commonly owned by the assignee of the present invention and the disclosure of which is hereby incorporated by reference, may then be used to secure the suture to barb 506, completing the bilateral capture. In this embodiment described herein, the skives are created simultaneously and the fastener 400 is inserted sequentially into each corresponding skive from an opposite direction. Alternatively, a single U-shaped needle could be utilized in place of pilot needles 154, 156 and both the skives and fastener could be created and inserted sequentially. Numerous other combinations of bilateral creation of skives and insertion of fasteners are contemplated by scope of the present invention.

As described herein, the fastener is oriented so that a working plane defined by the flexible body 502 of fastener 500 is substantially parallel to a plane generally defined by exterior surface 55 of epidermal layer 54, and transverse to vertical interface 51. Those of skill in the art will appreciate, however, that the working plane of fastener 500 could also be oriented substantially orthogonal, or oblique, with the plane generally defined by exterior surface 55 while remaining in a transverse orientation with respect to vertical interface 51. Those of skill in the art will also appreciate that other bilateral capture mechanical fastening systems wherein the target tissue zones are penetrated by a fastener in sequential fashion are possible within the scope of the present invention. For instance, a semi-circular, oval, or spiral fastener may be advanced sequentially through target tissue zones 70 on each side of vertical interface 51 using a mechanism that imparts a rotational motion to the fastener, but without causing interdigitation or overlapping of skin across vertical interface 51. The mechanism may have means for creating a semi-circular, oval or spiral skive through which the fastener may be advanced, or the fastener itself may be formed from sufficiently rigid material and have a sharpened point so as to be capable of creating a skive as it passes through the skin. In another alternative embodiment providing a sequential bilateral capture motion, a fastener is provided having a cross-member connecting two legs wherein the legs are staggered so that when the fastener is advanced into the skin in a linear fashion, one of the legs precedes the other. In still another embodiment, two straight fasteners comprising a shaft portion with skin-engaging barbs are provided. These fasteners are oriented in opposite directions on either side of the vertical interface 51, and are sequentially advanced through respective skives by an applicator assembly allowing a reversible motion.

Figure 22:
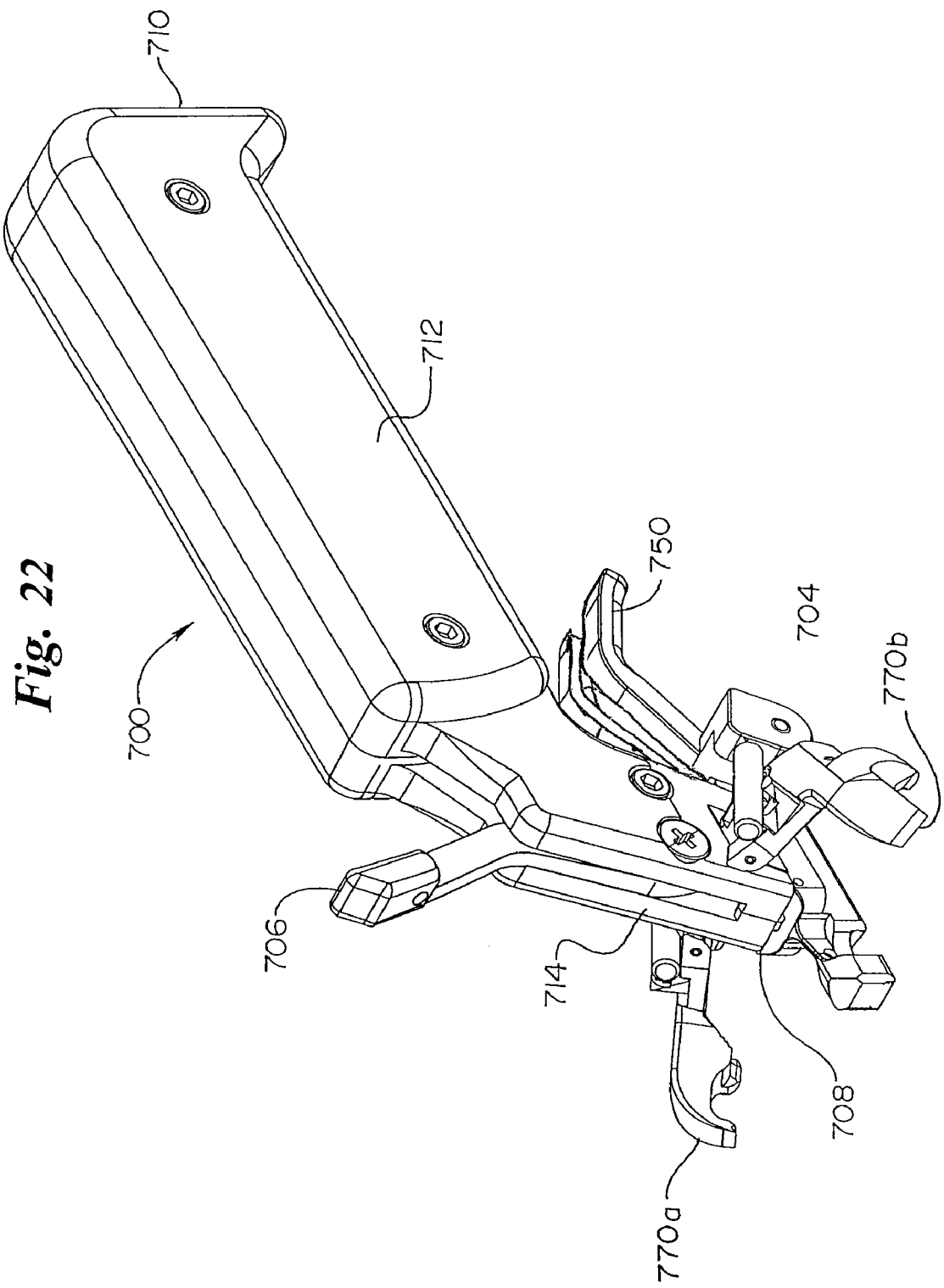
FIG. 22 is a perspective view of an embodiment of an applicator including a tissue manipulator assembly.
Figure 23:
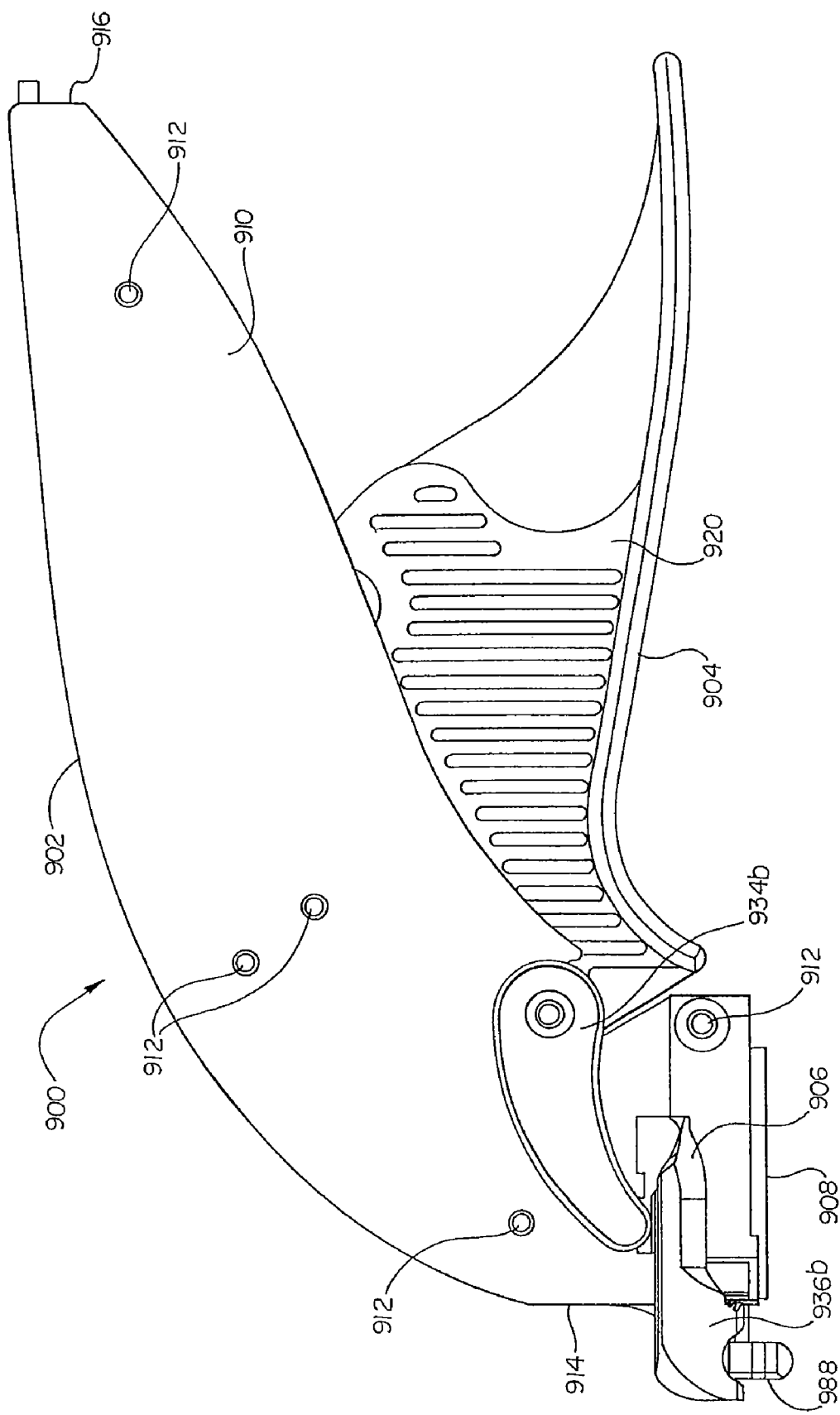
FIG. 23 is a perspective view of an embodiment of an applicator including a tissue manipulator assembly.

In alternative embodiments of an applicator apparatus, an applicator assembly can incorporate an integral tissue manipulator assembly, for example applicator assembly 700 as shown in FIG. 22 or applicator assembly 800 as shown in FIG. 23.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

What is claimed:

1. A mechanical method for securing skin tissue with a fastener comprising:
    positioning a mechanical apparatus such that a driving head portion is positioned in a vertical interface longer than a length of the fastener between a first tissue side and a second tissue side and at least partially below an exterior surface defined by epidermis tissue;
    approximating the first tissue side against the driving head portion with the mechanical apparatus such that a first target tissue zone is defined in the first tissue side,
    utilizing the mechanical apparatus to drive the fastener through the first target tissue zone such that the fastener is positioned below the exterior surface;
    approximating the second tissue side against the driving head portion with the mechanical apparatus such that a second target tissue zone is defined in the second tissue side; and
    utilizing the mechanical apparatus to drive the fastener through the second target tissue zone such that the fastener is positioned below the exterior surface and a portion of the fastener is positioned generally transverse to the vertical interface.

2. The method of claim 1, wherein the step of utilizing the mechanical apparatus to drive the fastener through the first target tissue zone is performed prior to the step of utilizing the mechanical apparatus to drive the fastener through the second target tissue zone such that the fastener is inserted sequentially into the first and second target tissue zones.

3. A mechanical method of fastening opposing skin tissue across an opening comprising:
    utilizing a manipulator apparatus to position a first side of the opposing skin tissue against a driving head to define a first target tissue zone and to position a second side of the opposing skin tissue against the driving head to define a second target tissue zone, each target tissue zone being defined in a plane of each dermal layer generally perpendicular to both a surface of the associated epidermal layer and a longitudinal orientation of the opening for a length longer than a length of the fastener; and
    utilizing the fastening apparatus to secure the dermal layers by inserting a fastener through each of the target tissue zones in an orientation generally perpendicular to the plane of the target tissue zones.

4. The method of claim 3, wherein the step of utilizing the fastening apparatus sequentially inserts the fastener first through one of the pair of target tissue zones and then through the other of the pair of target tissue zones.

5. The method of claim 4, wherein the step of utilizing the fastening apparatus sequentially inserts the fastener first through one of the pair of target tissue zones in a first direction parallel to the longitudinal orientation of the opening and then through the other of the pair of target tissue zones in an opposite direction parallel to the longitudinal orientation of the opening.

6. A mechanical method of fastening of a pair of opposing pieces of skin tissue across a gap comprising:
    utilizing a mechanical apparatus to position a dermal layer of each of the opposing skin tissue together at the gap such that a pair of unique tissue target zones in the dermal layer are presented, each tissue target zone being defined in a three dimensional volume of one of the pieces of opposing skin tissue at a depth of between 0.1 mm and 2.0 mm below an exterior surface of the skin tissue, at a width of between 1 mm and 20 mm from an edge of the gap and along a longitudinal length of the gap that is longer than a length of the fastener wherein the depth and width define an insertion plane generally perpendicular to the longitudinal length of the gap; and utilizing a fastening apparatus to secure the dermal layers by inserting a portion of a fastener through the insertion plane into each tissue target zone with no portion of the fastener above the exterior surface of the skin tissue.

7. The method of claim 6, wherein the step of utilizing the fastening apparatus sequentially inserts the fastener first through the insertion plane of one of the pair of target tissue zones and then through the insertion plane of the other of the pair of target tissue zones.

8. The method of claim 7, wherein the step of utilizing the fastening apparatus sequentially inserts the fastener first through the insertion plane of one of the pair of target tissue zones in a first direction parallel to the longitudinal orientation of the opening and then through the insertion plane of the other of the pair of target tissue zones in an opposite direction parallel to the longitudinal orientation of the opening.

\* \* \* \* \*

UNITED STATES PATENT AND TRADEMARK OFFICE
CERTIFICATE OF CORRECTION

PATENT NO. : 7,547,315 B2  Page 1 of 1
APPLICATION NO. : 11/003145
DATED : June 16, 2009
INVENTOR(S) : Peterson et al.

It is certified that error appears in the above-identified patent and that said Letters Patent is hereby corrected as shown below:

Column 2, Line 6:
After "3,792,010" insert --,--.

Column 4, Line 62:
After "have" delete "has".

Column 8, Line 62:
Delete "preferably" and insert --preferable--.

Column 9, Line 24:
After "head" delete "in" and insert --is--.

Column 12, Line 3:
Delete "issue" and insert --tissue--.

Signed and Sealed this

Twenty-fourth Day of August, 2010

David J. Kappos
*Director of the United States Patent and Trademark Office*